United States Patent [19]
Nishikawa et al.

[11] Patent Number: 5,679,834
[45] Date of Patent: Oct. 21, 1997

[54] PRODUCTION PROCESS OF (METH) ACRYLIC ACID ESTER HAVING BENZOIC ACID GROUP

[75] Inventors: Hideyuki Nishikawa, Minami Ashigara; Haruyoshi Gotou, Odawara, both of Japan

[73] Assignee: Fuji Photo Film Co., Ltd., Kanagawa, Japan

[21] Appl. No.: 616,197

[22] Filed: Mar. 15, 1996

[30] Foreign Application Priority Data

Mar. 16, 1995 [JP] Japan .................................. 7-057514

[51] Int. Cl.$^6$ .................................................... C07C 67/08
[52] U.S. Cl. ........................................................... 560/221
[58] Field of Search ............................................. 560/221

[56] References Cited

PUBLICATIONS

Broer et al. (1989) *Makromol.Chem.* 190, 2255–2268.
Portugall et al. (1982) *Makromol.Chem.* 183, 2311–2321.

*Primary Examiner*—Johann Richter
*Assistant Examiner*—Laura R. Cross
*Attorney, Agent, or Firm*—Birch, Stewart, Kolasch & Birch, LLP

[57] ABSTRACT

A process for producing an acrylic acid ester or a methacrylic acid ester having a benzoic acid group from a benzoic acid derivative having a hydroxyalkyl group in the presence of an acid catalyst without using an azeotropic solvent with water having a strong toxicity and also without using acrylic acid chloride which has a strong tearing property, is hard to be handled and generates a by-product in the reaction. In the above process, the solvent for the benzoic acid derivative consists essentially of (meth)acrylic acid.

10 Claims, No Drawings

PRODUCTION PROCESS OF (METH) ACRYLIC ACID ESTER HAVING BENZOIC ACID GROUP

FIELD OF THE INVENTION

The present invention relates to a production process for a (meth)acrylic acid ester containing an aromatic ring, which is used for a raw material for functional polymers such as polymer liquid crystals, etc.

BACKGROUND OF THE INVENTION

A process of producing a (meth)acrylic acid ester (i.e., an acrylic acid ester or a methacrylic acid ester) has been known in the art, and JP-B-60-42777 (the term "JP-B" as used herein means an "examined published Japanese patent application"), for example discloses a production process for a (meth)acrylic acid ester using (meth)acrylic acid and an alcohol in the presence of an acid catalyst. This process is applied to a process of producing a (meth)acrylic acid ester from a benzoic acid derivative having a hydroxyalkyl group and the process is described, e.g., in the research report by M. Portugall et al, *Makromol. Chem.*, Vol. 183, 2311 (1082). That is, a (meth)acrylic acid ester can be produced by the process of using an excessive amount of (meth)acrylic acid in the presence of chloroform which is an azeotropic solvent with water.

However, it is known that chloroform used in the process has a strong toxicity. In addition, benzene, which is generally known to be an azeotropic solvent with water at a temperature of not higher than 100° C. also has high toxicity.

Accordingly, a production technique for a (meth)acrylic acid ester without using solvents which have a strong toxicity has been desired.

In addition a process of using (meth)acrylic acid chloride for the production of (meth)acrylic acid ester is known as described in, for example, the research report by D. J. Broer et al, *Makromol. Chem.*, Vol. 190, 2255(1989).

However, in this process, (meth)acrylic acid chloride has a strong tearing property, and is difficult to handle. Furthermore, there is a problem that a by-product is generated in the reaction.

SUMMARY OF THE INVENTION

Accordingly, an object of the present invention is to provide a production process for the (meth)acrylic acid ester of a benzoic acid derivative having a hydroxyalkyl group, without using chloroform or benzene, which is an azeotropic solvent with water having high toxicity, and without using acrylic acid chloride which has a strong tearing property, is difficult to handle, and generates a by-product in the reaction.

Another object of the present invention is to provide a production process for the (meth)acrylic acid ester of a benzoic acid derivative having a hydroxyalkyl group which provides the desired product with a high yield.

The above objects of the present invention have been achieved by providing:

a process for producing an acrylic acid ester or a methacrylic acid ester having a benzoic acid group, comprising the steps of:

providing a benzoic acid derivative having a hydroxyalkyl group and an acid catalyst in a solvent; and esterifying the hydroxyl group in the hydroxyalkyl group, wherein the solvent for said benzoic acid derivative consists essentially of an acrylic or methacrylic acid.

DETAILED DESCRIPTION OF THE INVENTION

The present invention is described in detail below.

The molar amount of (meth)acrylic acid for use in the present invention is preferably from 1.0 times to 100 times, more preferably at least 5 times, and particularly preferably at least 10 times, the molar amount of a benzoic acid derivative having a hydroxyalkyl group. When the molar amount of (meth)acrylic acid is less than 5 times, the production ratio of a by-product is slightly increased, and when the molar amount thereof is not excessive, the production ratio of a by-product is markedly increased.

Examples of the acid catalyst for use in this invention include, for example, inorganic acids (e.g., hydrogen chloride and sulfuric acid); organic acids such as unsubstituted or substituted alkylsulfonic acids (e.g., methanesulfonic acid, trifluoromethanesulfonic acid), unsubstituted or substituted benzenesulfonic acids (e.g., p-toluenesulfonic acid, benzenesulfonic acid) and carboxylic acids (e.g., aromatic carboxylic acids such as perfluorobenzoic acid, and aliphatic carboxylic acids such as trifluoroacetic acid and trichloroacetic acid); and solid acids (e.g., amberlyst and activated clay). Of these catalysts, sulfuric acid and sulfonic acid derivatives are particularly preferred.

The addition amount of the acid catalyst for use in the process of the present invention is preferably from 0.1 to 200 mol %, and more preferably from 0.5 to 50 mol % based on the molar amount of the benzoic acid derivative having a hydroxyalkyl group. The amount of the acid catalyst only influences the reaction rate. For example, when the addition amount is less than 0.1 mol %, a long time is required until the reaction is finished.

One of the features of the process of the present invention resides in that it does not utilize any common solvents such as alcohol solvents (e.g., methanol, ethanol and isopropanol), aromatic solvents (e.g., benzene, toluene and pyridine), ether solvents (e.g., diethyl ether and tetrahydrofuran), ester solvents (e.g., ethyl acetate), halogenous solvents (e.g., dichloromethane, chloroform), ketone solvents (e.g., acetone), hydrocarbon solvents having a straight chain (e.g., hexane and pentane) and aprotic solvents (e.g., dimethylformamide and dimethyl sulfoxide).

The reaction temperature is generally from 30° to 100° C., and preferably from 50° to 80° C.

It is not always necessary to remove water generated in the reaction from the reaction system. However, when the residues of the raw material cause a problem, removal of the water is preferably carried out. In this case, a method of removing water together with (meth)acrylic acid from the system after the reaction reaches the equilibrium may be used. In removing water from the system, the removal is preferably carried out under a reduced pressure to control the temperature to a preferred temperature of from 50° to 80° C.

In the process of the present invention, a polymerization inhibitor may be used. Examples of the polymerization inhibitor include those generally used as the polymerization inhibitor for (meth)acrylic acid, such as phenothiazine, hydroquinone, hydroquinone monomethyl ether, nitrobenzene, t-butylcatechol, etc., as well as inorganic salts such as copper chloride, copper sulfide, etc. The addition amount of the polymerization inhibitor is preferably from 10 to 10,000 ppm by weight, particularly preferably from 100 to 1,000 ppm by weight, based on the weight of the (meth)acrylic acid used in the process of the present invention.

The benzoic acid derivative having a hydroxyalkyl group for use in the present invention is a benzoic acid substituted by a substituent containing a hydroxyalkyl group. As the substituent containing a hydroxyalkyl group, any substituents containing a hydroxyalkyl group may be used. For example, the substituent may further contain an aryl group or a heterocyclic group, or may have a functional group such as an ether group, an ester group, a carbonyl group, a thioether group, a sulfoxide group, a sulfonyl group, an amido group, etc. Furthermore, the hydroxyalkyl group may be substituted by a substituent such as, for example, an alkoxy group, an alkyl group, an alkoxycarbonyl group and a halogen atom. The alkoxy group, the alkyl group and the alkoxycarbonyl group preferably has from 1 to 20 carbon atoms, particularly preferably from 1 to 10 carbon atoms.

The benzoic acid substituted with a substituent containing a hydroxyalkyl group may be further substituted with other substituents such as, for example, an alkoxy group, an alkyl group, an alkoxycarbonyl group, a nitro group, and a halogen atom. The alkoxy group, the alkyl group and the alkoxycarbonyl group preferably has from 1 to 20 carbon atoms, particularly preferably from 1 to 10 carbon atoms.

The benzoic acid derivative having a hydroxyalkyl group for use in the present invention is preferably a compound represented by following formula (I):

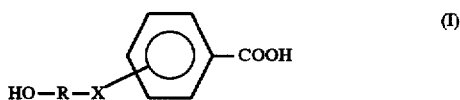

wherein R represents an alkylene group and X represents an oxygen atom or a sulfur atom.

Then, the compound represented by the above described formula (I) is described in detail below.

The alkylene group represented by R in the formula (I) may be unsubstituted or substituted, and generally has from 2 to 30 carbon atoms, preferably from 2 to 20 carbon atoms.

Examples of the unsubstituted alkylene group include ethylene, propylene, butylene, pentylene, hexylene, heptylene, octylene, nonylene, decylene, 2-ethylbutylene and 3-ethylbutylene. Examples of the substituent for the substituted alkylene group include, for example, an acylamino group, an alkoxy group, a vinyl group, a phenyl group, an acyloxy group, an alkylthio group, an alkoxycarbonyl group, an acyl group and a halogen atom. Of these, the acylamino group, the alkoxy group, the acyloxy group, the alkylthio group, the alkoxycarbonyl group and the acyl group preferably has from 1 to 20 carbon atoms, particularly preferably from 1 to 10 carbon atoms. Specifically, examples of the substituted alkylene group include 3-methoxybutylene, 2-acetoxypropylene, 2-methylthiobutylene, 4-methoxycarbonylhexylene, 3-acetylbutylene and 5-chlorohexylene.

In addition, the carbon atom of the alkylene group may be replaced with other atom such as, for example, an oxygen atom (e.g., 2-ethyleneoxyethylene) and a sulfur atom (e.g., 2-ethylenethioethylene).

X may be substituted at any position of the aromatic ring.

Specific examples of the benzoic acid derivative having a hydroxyalkyl group for use in the present invention and the compound obtained by the process of this invention are shown below, but the invention is not limited thereto. In addition, in the following compounds, compounds where Q=H are the compounds represented by the formula (I) of this invention and other compounds are desired ester compounds obtained by the process of this invention.

| n | X | Q=H | Q=CH$_2$=CH—CO— | Q = $\overset{CH_3}{\underset{CH_2}{>}}$C—CO— |
|---|---|---|---|---|
| | | | Q—O—(CH$_2$)$_n$—X—C$_6$H$_4$—COOH | |
| 2 | O | No. 1 | No. 19 | No. 37 |
| 3 | O | No. 2 | No. 20 | No. 38 |
| 4 | O | No. 3 | No. 21 | No. 39 |
| 5 | O | No. 4 | No. 22 | No. 40 |
| 6 | O | No. 5 | No. 23 | No. 41 |
| 7 | O | No. 6 | No. 24 | No. 42 |
| 8 | O | No. 7 | No. 25 | No. 43 |
| 9 | O | No. 8 | No. 26 | No. 44 |
| 10 | O | No. 9 | No. 27 | No. 45 |
| 2 | S | No. 10 | No. 28 | No. 46 |
| 3 | S | No. 11 | No. 29 | No. 47 |
| 4 | S | No. 12 | No. 30 | No. 48 |
| 5 | S | No. 13 | No. 31 | No. 49 |
| 6 | S | No. 14 | No. 32 | No. 50 |
| 7 | S | No. 15 | No. 33 | No. 51 |
| 8 | S | No. 16 | No. 34 | No. 52 |
| 9 | S | No. 17 | No. 35 | No. 53 |
| 10 | S | No. 18 | No. 36 | No. 54 |
| | | | Q—O—(CH$_2$CH$_2$O)$_n$—CH$_2$CH$_2$—X—C$_6$H$_4$—COOH | |
| 0 | O | No. 55 | No. 61 | No. 67 |
| 1 | O | No. 56 | No. 62 | No. 68 |
| 2 | O | No. 57 | No. 63 | No. 69 |

-continued

| | | | | |
|---|---|---|---|---|
| 0 | S | No. 58 | No. 64 | No. 70 |
| 1 | S | No. 59 | No. 65 | No. 71 |
| 2 | S | No. 60 | No. 66 | No. 72 |

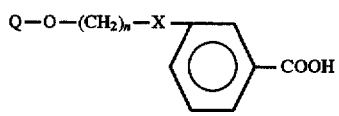

| | | | | |
|---|---|---|---|---|
| 2 | O | No. 73 | No. 91 | No. 109 |
| 3 | O | No. 74 | No. 92 | No. 110 |
| 4 | O | No. 75 | No. 93 | No. 111 |
| 5 | O | No. 76 | No. 94 | No. 112 |
| 6 | O | No. 77 | No. 95 | No. 113 |
| 7 | O | No. 78 | No. 96 | No. 114 |
| 8 | O | No. 79 | No. 97 | No. 115 |
| 9 | O | No. 80 | No. 98 | No. 116 |
| 10 | O | No. 81 | No. 99 | No. 117 |
| 2 | S | No. 82 | No. 100 | No. 118 |
| 3 | S | No. 83 | No. 101 | No. 119 |
| 4 | S | No. 84 | No. 102 | No. 120 |
| 5 | S | No. 85 | No. 103 | No. 121 |
| 6 | S | No. 86 | No. 104 | No. 122 |
| 7 | S | No. 87 | No. 105 | No. 123 |
| 8 | S | No. 88 | No. 106 | No. 124 |
| 9 | S | No. 89 | No. 107 | No. 125 |
| 10 | S | No. 90 | No. 108 | No. 126 |

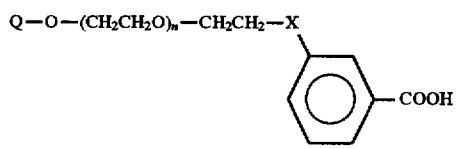

| | | | | |
|---|---|---|---|---|
| 0 | O | No. 127 | No. 133 | No. 139 |
| 1 | O | No. 128 | No. 134 | No. 140 |
| 2 | O | No. 129 | No. 135 | No. 141 |
| 0 | S | No. 130 | No. 136 | No. 142 |
| 1 | S | No. 131 | No. 137 | No. 143 |
| 2 | S | No. 132 | No. 138 | No. 144 |

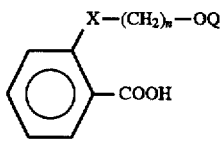

| | | | | |
|---|---|---|---|---|
| 2 | O | No. 145 | No. 163 | No. 181 |
| 3 | O | No. 146 | No. 164 | No. 182 |
| 4 | O | No. 147 | No. 165 | No. 183 |
| 5 | O | No. 148 | No. 166 | No. 184 |
| 6 | O | No. 149 | No. 167 | No. 185 |
| 7 | O | No. 150 | No. 168 | No. 186 |
| 8 | O | No. 151 | No. 169 | No. 187 |
| 9 | O | No. 152 | No. 170 | No. 188 |
| 10 | O | No. 153 | No. 171 | No. 189 |
| 2 | S | No. 154 | No. 172 | No. 190 |
| 3 | S | No. 155 | No. 173 | No. 191 |
| 4 | S | No. 156 | No. 174 | No. 192 |
| 5 | S | No. 157 | No. 175 | No. 193 |
| 6 | S | No. 158 | No. 176 | No. 194 |
| 7 | S | No. 159 | No. 177 | No. 195 |
| 8 | S | No. 160 | No. 178 | No. 196 |
| 9 | S | No. 161 | No. 179 | No. 197 |
| 10 | S | No. 162 | No. 180 | No. 198 |

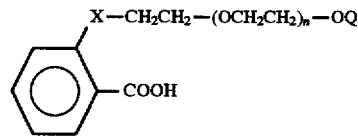

| | | | | |
|---|---|---|---|---|
| 0 | O | No. 199 | No. 205 | No. 211 |
| 1 | O | No. 200 | No. 206 | No. 212 |
| 2 | O | No. 201 | No. 207 | No. 213 |
| 0 | S | No. 202 | No. 208 | No. 214 |

-continued

| | | | | |
|---|---|---|---|---|
| 1 | S | No. 203 | No. 209 | No. 215 |
| 2 | S | No. 204 | No. 210 | No. 216 |

| | Q=H | Q=CH₂=CH—CO— | 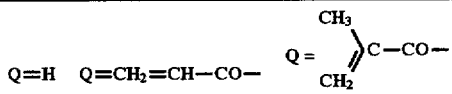 |
|---|---|---|---|
| QOCH₂CH₂O—⟨⟩—COO—⟨⟩—COOH | No. 217 | No. 218 | No. 219 |
| QO—CH₂CH₂O—⟨⟩—⟨⟩—COOH | No. 220 | No. 221 | No. 222 |
| QO—CH₂CH₂O—⟨N⟩—CO₂—⟨⟩—COOH | No. 223 | No. 224 | No. 225 |
| QO(CH₂)₄—⟨⟩—COOH | No. 226 | No. 227 | No. 228 |
| QO(CH₂)₄—O—C(=O)—⟨⟩—COOH | No. 229 | No. 230 | No. 231 |
| QO(CH₂)₄—C(=O)—NH—⟨⟩—COOH | No. 232 | No. 233 | No. 234 |
| QO—CH₂CH₂—S(=O)—⟨⟩—COOH | No. 235 | No. 236 | No. 237 |
| QO—CH₂CH₂—C(=O)—⟨⟩—COOH | No. 238 | No. 239 | No. 240 |

| Z | Q=H | Q=CH₂=CH—CO— | $Q = \begin{matrix}CH_3\\CH_2\end{matrix}\!\!\!\!\!>\!\!C\text{—CO—}$ |
|---|---|---|---|

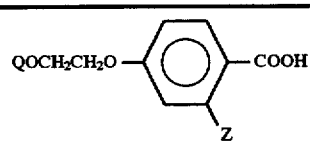

| Z | Q=H | Q=CH₂=CH—CO— | |
|---|---|---|---|
| —CH₃ | No. 241 | No. 242 | No. 243 |
| —C₂H₅ | No. 244 | No. 245 | No. 246 |
| —OCH₃ | No. 247 | No. 248 | No. 249 |
| —OC₂H₅ | No. 250 | No. 251 | No. 252 |
| —CO₂CH₃ | No. 253 | No. 254 | No. 255 |
| —OC(=O)CH₃ | No. 256 | No. 257 | No. 258 |
| —NO₂ | No. 259 | No. 260 | No. 261 |
| —F | No. 262 | No. 263 | No. 264 |
| —Cl | No. 265 | No. 266 | No. 267 |
| —Br | No. 268 | No. 269 | No. 270 |
| —I | No. 271 | No. 272 | No. 273 |

-continued

| | QOCH₂CHCH₂CH₂O—⟨phenyl⟩—COOH<br>Z | | |
|---|---|---|---|
| —OCH₃ | No. 274 | No. 275 | No. 276 |
| —OC₂H₅ | No. 277 | No. 278 | No. 279 |
| $-\text{OCCH}_3$ (O=) | No. 280 | No. 281 | No. 282 |
| —CH=CH₂ | No. 283 | No. 284 | No. 285 |
| —phenyl | No. 286 | No. 287 | No. 288 |
| $-\text{C(=O)CH}_3$ | No. 289 | No. 290 | No. 291 |
| —SCH₃ | No. 292 | No. 293 | No. 294 |
| —CO₂CH₃ | No. 295 | No. 296 | No. 297 |
| —NHCCH₃ (O=) | No. 298 | No. 299 | No. 300 |
| —Br | No. 301 | No. 302 | No. 303 |

The present invention will be described in more detail below with reference to the following Examples and comparative Examples, but the invention should not be construed as being limited thereto.

EXAMPLE 1

(Synthesis of Compound No. 21)

In a 300 ml round-bottom flask were placed 140 g (20 mol) of acrylic acid, 0.98 g (0.01 mol) of sulfuric acid, 0.50 g of hydroquinone monomethyl ether and 21.0 g (1 mol) of Compound No. 3, and allowed to react for 7 hours at 65° C. After cooling, the reaction mixture was poured in 500 ml of water and crystals formed were recrystallized from an acetone/water solvent to obtain 21.9 g (Yield: 83%) of Compound No. 21.

(Identification data of Compound No. 21)

¹H-NMR(CDCl₃) δ: 8.1(d,2H), 6.9(d,2H), 6.4(d,1H), 6.1 (dd,1H), 5.8 (d,1H), 4.2(t,2H), 4.0(t,2H), 1.6–1.9(m,4H)

Melting point: 120° to 122° C.

EXAMPLE 2

(Synthesis of Compound No. 21)

After carrying out the reaction for 7 hours at 65° C. in the same manner as in Example 1, a mixed liquid of water and acrylic acid was removed at 65° C. over a period of 2 hours under reduced pressure. After cooling, the reaction mixture was poured in 500 ml of water and crystals formed were collected by filtration under reduced pressure, washed with water, and air-dried to obtain 25.1 g (Yield: 95%) of Compound No. 21.

EXAMPLE 3

(Synthesis of Compound No. 22)

The same procedures as in Example 2 were carried out except that Compound No. 3 was replaced with Compound 4 to obtain 26.4 g (Yield: 95%) of Compound No. 22.

(Identification date of Compound No. 22)

¹H-NMR(CDCl₃) δ: 8.1(d,2H), 6.9(d,2H), 6.4(d,1H), 6.1 (dd,1H), 5.8(d,1H), 4.2(t,2H), 4.0(t,2H), 1.6–1.9(m,4H), 1.4–1.6(m,2H)

Phase transition temperature: (Crystal phase)-(99° C.)-(liquid crystal phase)-(112° C.)-(isotropic liquid)

EXAMPLE 4

(Synthesis of Compound No. 23)

The same procedures as in Example 2 were carried out except that Compound No. 3 was replaced with Compound 5 to obtain 27.4 g (Yield: 94%) of Compound No. 23.

(Identification date of Compound No. 23)

¹H-NMR(CDCl₃) δ: 8.1(d,2H), 6.9(d,2H), 6.4(d,1H), 6.1 (dd,1H), 5.8(d,1H), 4.2(t,2H), 4.0(t,2H), 1.6–1.9(m,4H), 1.4–1.6(m,4H)

Phase transition temperature: (Crystal phase)-(89° C.)-(liquid crystal phase)-(113° C.)-(isotropic liquid)

EXAMPLE 5

(Synthesis of Compound No. 25)

The same procedures as in Example 2 were carried out except that Compound No. 3 was replaced with Compound 7 to obtain 30.4 g (Yield: 95%) of Compound No. 25.

(Identification data of Compound No. 25)

¹H-NMR(CDCl₃) δ: 8.1(d,2H), 6.9(d,2H), 6.4(d,1H), 6.1 (dd,1H), 5.8(d,1H), 4.2(t,2H), 4.0(t,2H), 1.6–1.9(m,4H), 1.4–1.6(m,8H)

Phase transition temperature: (Crystal phase)-(75° C.)-(liquid crystal phase)-(112° C.)-(isotropic liquid)

EXAMPLE 6

(Synthesis of Compound No. 26)

The same procedures as in Example 2 were carried out except that Compound No. 3 was replaced with Compound 8 to obtain 31.4 g (Yield: 94%) of Compound No. 26.

11

(Identification data of Compound No. 26)
$^1$H-NMR(CDCl$_3$) δ: 8.1(d,2H), 6.9(d,2H), 6.4(d,2H), 6.1 (dd,1H), 5.8(d,1H), 4.2(t,2H), 4.0(t,2H), 1.6–1.9(m,4H), 1.3–1.6(m,10H)

Phase transition temperature: (Crystal phase)-(99° C.)-(liquid crystal phase)-(115° C.)-(isotropic liquid)

EXAMPLE 7

(Synthesis of Compound No. 41)

The same procedures as in Example 2 were carried out except that Compound No. 3 and acrylic acid were each replaced with Compound 56 and methacrylic acid, respectively, to obtain 26.5 g (Yield: 96%) of Compound No. 41.

(Identification data of Compound No. 41)
$^1$H-NMR(CDCl$_3$) δ: 8.1(d,2H), 6.9(d,2H), 6.1(s,1H), 5.5 (s,1H), 4.2(t,2H), 4.0(t,2H), 1.9(s,3H), 1.6–1.9(m,4H), 1.4–1.6(m,4H)

Phase transition temperature: (Crystal phase)-(65° C.)-(liquid crystal phase)-(100° C.)-(isotropic liquid)

EXAMPLE 8

(Synthesis of Compound 62)

The same procedures as in Example 2 were carried out except that Compound No. 3 was replaced with Compound 56 to obtain 25.8 g (Yield: 92%) of Compound No. 62.

(Identification data of Compound No. 62)
$^1$H-NMR(CDCl$_3$) δ: 7.9(d,2H), 7.0(d,2H), 6.4(d,1H), 6.2 (dd,1H), 5.9(d,1H), 4.3(t,2H), 4.2(t,2H), 3.8(t,2H), 3.7(t,2H)

Melting point: 156°–158° C.

Comparative Example 1

(Synthesis of Compound No. 21)

In this Comparative Example, toluene was used as an azeotropic solvent.

In a 500 ml round-bottom flask were placed 140 g (20 mol) of acrylic acid, 1.0 g of p-toluenesulfonic acid, 0.50 g of hydroquinone monomethyl ether, 21.0 g (1.0 mol) of Compound No. 3 and 100 ml of toluene, and allowed to react for one hour at a reaction temperature of 120° C. Water generated accompanying with the esterification was removed from the system by the azeotropic distillation with toluene. Also, toluene separated from water was put back into the reaction system.

Many white insoluble matters, which were considered to be polymers, were attached to the walls of the flask after the reaction (Yield of Compound No. 21: 76%).

Comparative Example 2

(Synthesis of Compound No. 2)

In this comparative Example, hexane was used as an azeotropic solvent.

In a 500 ml round-bottom flask were placed 140 g (20 mol) of acrylic acid, 1.0 g of p-toluenesulfonic acid, 0.50 g of hydroquinone monomethyl ether, 21.0 g (1.0 mol) of Compound No. 3 and 100 ml of n-hexane, and allowed to react for 6 hours at a reaction temperature of 80° C. Water generated accompanying with the esterification was removed from the system by the azeotropic distillation with n-hexane. Also, n-hexane separated from water was put back into the reaction system. In the reaction system, there remained crystals of Compound No. 21 as undissolved (Yield of Compound No. 21: 23%).

12

Comparative Example 3

(Synthesis of Compound No. 21)

In this comparative Example, acrylic acid chloride was used.

Using acrylic acid chloride and Compound No. 3, the synthesis was carried out according to the synthesis process described in the research report by D. J. Broer et al, Makromol. Chem., Vol. 190, 2255 (1989). (Yield of Compound No. 21: 83%)

Comparative Example 4

(Synthesis of Compound No. 21)

In this comparative Example, acrylic acid was used in the equivalent molar amount to that of a benzoic acid derivative having a hydroxyalkyl group.

In a 200 ml round-bottom flask were placed 7.0 g (1.0 mol) of acrylic acid, 1.0 g of p-toluenesulfonic acid, 0.50 g of hydroquinone monomethyl ether, 21.0 g (1.0 mol) of Compound No. 3 and 100 ml of chloroform, and allowed to react for 12 hours at a reaction temperature of 65° C. Water generated accompanying with the esterification was removed from the system by the azeotropic distillation with chloroform. Also, chloroform separated from water was put back into the reaction system. (Yield of Compound No. 21: 75%)

The above results are shown in Table 1 below. In addition, the selectivity was obtained by HPLC (eluent: THF/H$_2$O= 50/50, detection wavelength: 254 nm) with sampling the reaction mixture.

TABLE 1

| | Desired Product | By-Product by Addition of Hydrochloric Acid | Raw Material Hydroxy Compound | By-Product Originated in Dimerization | Isolation Yield |
|---|---|---|---|---|---|
| Ex. 1 | 94.7% | 0% | 2.5% | 0.5% | 83% |
| Ex. 2 | 96.0% | 0% | 0.2% | 0.6% | 95% |
| Comp. Ex.1 | 93.7% | 0% | 2.1% | 0.8% | 76% |
| Comp. Ex.2 | 27.3% | 0% | 71.8% | 0.3% | 23% |
| Comp. Ex.3 | 93.6% | 2.9% | 0.2% | 0% | 83% |
| Comp. Ex.4 | 79.2% | 0% | 3.3% | 13.0% | 75% |

Ex.: Example of this invention
Comp. Ex.: Comparative Example

From the results shown in Table 1, the selectivity of the desired product is good and further, the isolation yield is also good in the examples of the present invention.

On the other hand, in Comparative Examples 1 and 2 using toluene and n-hexane, respectively, the isolation yield is lowered by the reasons of the polymerization and the solubility of a hydroxy compound as the raw material.

Also, in Comparative Example 3 using acrylic acid chloride, the selectivity of the desired product and the amount of the by-product are inferior in the case of the present invention.

Furthermore, in Comparative Example 4 using the equivalent amount of acrylic acid, the formation of a by-product originated in the dimerization is increased and the yield of the desired product is decreased with the increase of the by-product.

As described above, the present invention provides a production process for the (meth)acrylic acid ester of a benzoic acid derivative having a hydroxyalkyl group without using chloroform and benzene, each being an azeotropic solvent with water having a high toxicity, and without using acrylic acid chloride which has a strong tearing property, is difficult to handle, and generates a by-product by the reaction.

While the invention has been described in detail and with reference to specific examples thereof, it will be apparent to one skilled in the art that various changes and modifications can be made therein without departing from the spirit and scope thereof.

What is claimed is:

1. A process for producing an acrylic acid ester or a methacrylic acid ester having a benzoic acid group, comprising the steps of:

providing a benzoic acid derivative having a hydroxyalkyl group and an acid catalyst in a solvent; and esterifying the hydroxyl group in said hydroxyalkyl group;

wherein said solvent for said benzoic acid derivative consists essentially of an acrylic or methacrylic acid.

2. The process for producing an acrylic acid ester or a methacrylic acid ester as claimed in claim 1, wherein said benzoic acid derivative having a hydroxyalkyl group is a compound represented by following formula (I):

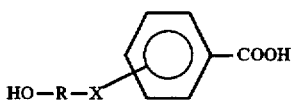

wherein R represents an alkylene group and X represents an oxygen atom or a sulfur atom.

3. The process for producing an acrylic acid ester or a methacrylic acid ester as claimed in claim 1, wherein said acrylic or methacrylic acid is used in a molar amount of from more than 1.0 times to not more than 100 times the molar amount of said benzoic acid derivative having a hydroxyalkyl group.

4. The process for producing an acrylic acid ester or a methacrylic acid ester as claimed in claim 3, wherein said acrylic or methacrylic acid is used in a molar amount of from not less than 5 times to not more than 100 times the molar amount of said benzoic acid derivative having a hydroxyalkyl group.

5. The process for producing an acrylic acid ester or a methacrylic acid ester as claimed in claim 4, wherein said acrylic or methacrylic acid is used in a molar amount of from not less than 10 times to not more than 100 times the molar amount of said benzoic acid derivative having a hydroxyalkyl group.

6. The process for producing an acrylic acid ester or a methacrylic acid ester as claimed in claim 1, wherein said acid catalyst is used in an amount of from 0.1 to 200 mol % based on the molar amount of said benzoic acid derivative.

7. The process for producing an acrylic acid ester or a methacrylic acid ester as claimed in claim 6, wherein said acid catalyst is used in an amount of from 0.5 to 50 mol % based on the molar amount of said benzoic acid derivative.

8. The process for producing an acrylic acid ester or a methacrylic acid ester as claimed in claim 1, wherein said esterifying step is conducted at a temperature of from 30° to 100° C.

9. The process for producing an acrylic acid ester or a methacrylic acid ester as claimed in claim 8, wherein said esterifying step is conducted at a temperature of from 50° to 80° C.

10. The process for producing an acrylic acid ester or a methacrylic acid ester as claimed in claim 2, wherein said alkylene group represented by R has from 2 to 30 carbon atoms.

* * * * *